United States Patent
Zappala

(10) Patent No.: US 6,364,855 B1
(45) Date of Patent: Apr. 2, 2002

(54) MULTILUMEN URETHRAL CATHETER FOR TRANSPERINEAL BRACHYTHERAPY

(76) Inventor: Stephen M. Zappala, 98 Rattlesnake Rd., Andover, MA (US) 01810

( * ) Notice: Subject to any disclaimer, the term of this patent is extended or adjusted under 35 U.S.C. 154(b) by 0 days.

(21) Appl. No.: 09/652,177

(22) Filed: Aug. 31, 2000

Related U.S. Application Data

(60) Provisional application No. 60/151,903, filed on Sep. 1, 1999.

(51) Int. Cl.[7] .............................................. A61M 29/00
(52) U.S. Cl. ...................................... 604/96.01; 604/48
(58) Field of Search ......................... 604/48, 502, 514, 604/57, 93.01, 96.01, 99.02, 103.1, 264, 523, 529, 285

(56) References Cited

U.S. PATENT DOCUMENTS 4,364,392 A * 12/1982 Strother et al. ............. 606/195
6,030,362 A * 2/2000 Boussignac et al.
6,099,457 A * 8/2000 Good

* cited by examiner

Primary Examiner—Sharon Kennedy
Assistant Examiner—Catherine Serke
(74) Attorney, Agent, or Firm—Mirick, O'Connell, DeMallie & Lougee, LLP

(57) ABSTRACT

A urethral catheter adapted to facilitate transperineal brachytherapy, comprising, a sleeve having a proximal end, a distal end and at least one lumen filled with a masma comprising a plurality of hypoechoic microspheres; an inflatable balloon fixed about the sleeve proximate the distal end; an inflation valve proximate the proximal end; and a channel, integral with at least a portion of the sleeve, for transporting an inflation medium from the valve to the balloon.

13 Claims, 3 Drawing Sheets

MULTILUMEN URETHRAL CATHETER FOR TRANSPERINEAL BRACHYTHERAPY

This application claims benefit of Prov. No. 60/151,903 filed Sep. 1, 1999.

FIELD OF THE INVENTION

This invention relates to devices used in transperineal brachytherapy and more specifically to a urethral catheter that contains hypoechoic microspheres that are recognizable by transrectal ultrasonography (TRUS).

BACKGROUND OF THE INVENTION

Prostate cancer is one of the most common cancers in men. One often used treatment for localized prostate cancer is transperineal brachytherapy. Transperineal brachytherapy involves the delivery of an implantable radioactive delivery source to the prostate while limiting exposure to adjacent tissues. Delivery is achieved by implanting radioactive "seeds" directly into the prostatic stroma. The seeds typically comprise a radioactive isotope, such as Iodine 125, Palladium 103 or iridium. The accuracy of the implantation is critical to avoid damaging surrounding tissues, postoperative morbidity and potential urologic complications. However, accurate placement of the radioactive material is highly dependent on the skill of the surgeon and the surgeon's ability to identify anatomic landmarks such as the posterior urethra, bladder neck and external urinary sphincter. The surgeon's ability to visualize the internal topography of the patient's organs and tissues depends, in part, on the equipment used. The internal topography is typically visualized, and the implantation guided, by transrectal ultrasonography (TRUS). However, the usefulness of transrectal ultrasonography is limited by the less than optimal acoustic properties of the human anatomy.

SUMMARY OF THE INVENTION

It is therefore a primary object of this invention to provide a urethral catheter which compliments and facilitates transperineal brachytherapy in the management of localized prostate cancer.

It is a further object of this invention to provide a urethral catheter which contains hypoechoic microspheres that are recognizable by transrectal ultrasonography.

It is a further object of this invention to provide a urethral catheter which includes a plurality of hyperechoic markers along its length to allow a surgeon to accurately determine prostatic urethral lengths.

It is a further object of the invention to provide a catheter which improves the surgeon's ability to identify critical anatomic landmarks using transrectal ultrasonography.

It is a further object of the invention to provide a urethral catheter for transperineal brachytherapy which is disposable.

It is a further object of the invention to provide a device which increases the surgeon's ability to accurately determine the location of the bladder neck and external urinary sphincter during transperineal brachytherapy to properly distribute the implanted radioactive material uniformly to enhance the clinical outcome of the treatment.

It is a further object of this invention to provide a urethral catheter which reduces postoperative morbidity and potential urologic complications associated with transperineal brachytherapy.

A preferred embodiment of the urethral catheter of the invention, which is adapted to facilitate transperineal brachytherapy, generally comprises: a sleeve having a proximal end, a distal end and at least one lumen at least partially filled with a masma comprising a plurality of hypoechoic microspheres; an inflatable balloon fixed about the sleeve proximate the distal end; an inflation valve proximate the proximal end; and a channel, integral with at least a portion of the sleeve, for transporting an inflation medium from the valve to the balloon. The sleeve preferably defines an outer wall and an inner wall defining at least said one inner lumen that is at least partially filled with a masma comprising a plurality of hypoechoic microspheres, wherein the channel is interposed between the outer wall and the inner wall. The sleeve is preferably made of latex and the entire catheter is preferably disposable after just a single use.

The inflation medium may comprise one or more gaseous components, and/or one or more fluids; wherein the balloon is preferably adapted to be inflated with the inflation medium to a volume of about 5 cubic centimeters.

The plurality of microspheres are adapted to appear sufficiently hypoechoic to create an acoustic shadow when viewed by transrectal ultrasound. In addition to the hypoechoic microsphere, the sleeve may further comprise one or more hyperechoic markers between the distal end and the proximal end, wherein the hyperechoic markers may comprise circumferential ribs that are integral with the sleeve and are provided at 1 centimeter (cm) intervals.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS

The invention features a urethral catheter that is designed to complement the surgical procedure known commonly as transperineal brachytherapy and to potentially enhance the clinical outcomes of brachytherapy. The catheter is designed to be a single use, disposable catheter. Although other suitable materials may be used, including materials that are suited to disposable and/or non-disposable applications, the catheter is preferably made of a disposable latex. The catheter features an inflatable balloon at the distal/bladder end and a central lumen containing a semisolid masma comprising a plurality of hypoechoic, gas-filled microspheres.

The hypoechoic microspheres improve the identification of the prostatic urethra by transrectal ultrasonography (TRUS). The gas-filled microspheres have a unique ultrasound character that is readily recognized by an experienced physician. The acoustic image of the microspheres is a dark, hypoechoic image with acoustic shadowing. The TRUS appearance of the structural interface between the featured urethral catheter and the prostate improves the identification of the critical, albeit constant, anatomic landmarks. The catheter may also contain, beginning near the distal end, hyperechoic markers at one centimeter (cm) intervals to enable the physician to accurately determine prostatic urethral lengths.

The catheter is adapted to be inserted through the male urethral meatus and directed into the urinary bladder in a manner and fashion conventional with urethral catheterization. The balloon is inflated once the catheter is inside of the bladder, and with gentle traction, the balloon is manipulated to the level of the bladder neck.

Figure 1:
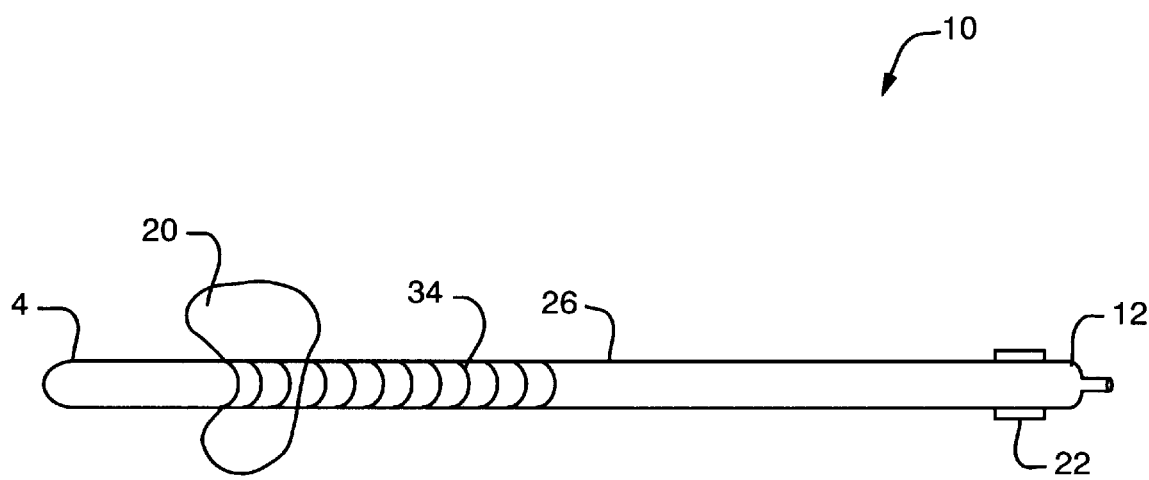
FIG. 1 is a side view of the preferred embodiment of the catheter of this invention.
Figure 4:
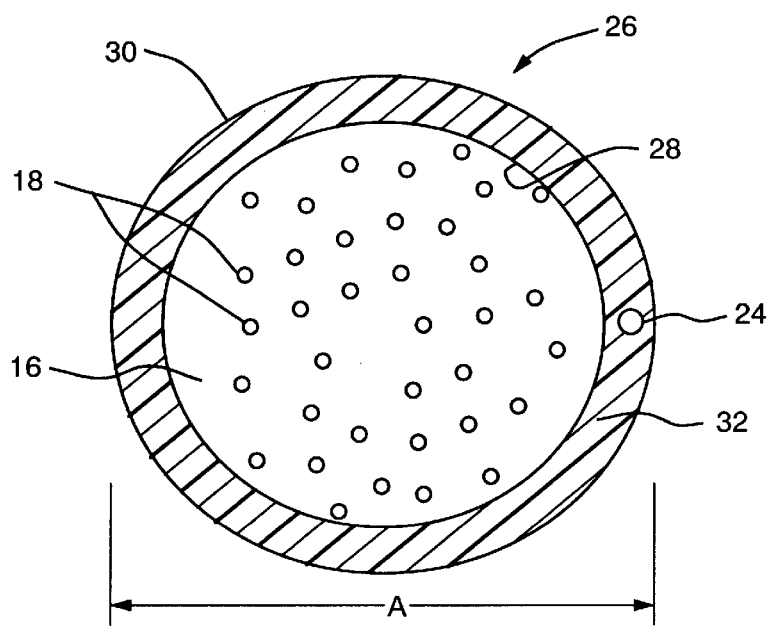
FIG. 4 is cross-sectional view of the catheter of the invention.

The preferred embodiment of the catheter of the invention is shown in FIGS. 1 and 4 and referred to as catheter 10. Catheter 10 generally comprises: a sleeve 26 having a proximal end 12, a distal (terminal) end 14 and at least one lumen 16 filled with a masma comprising a plurality of hypoechoic microspheres 18; an inflatable balloon 20 fixed about the sleeve 26 proximate the distal end 14; an inflation valve 22 proximate the proximal end 12; and a channel 24, integral with at least a portion of the sleeve 26, for transporting an inflation medium from the valve 22 to the balloon 20. The sleeve 26 defines an outer wall 30 and an inner wall 28. Channel 24 is interposed in, and extends through, a portion of an annular space located between outer wall 30 and inner wall 28. Inner wall 28 surrounds inner lumen 16. Sleeve 26 is preferably made of latex and the entire catheter is disposable after just a single use.

Figure 2:
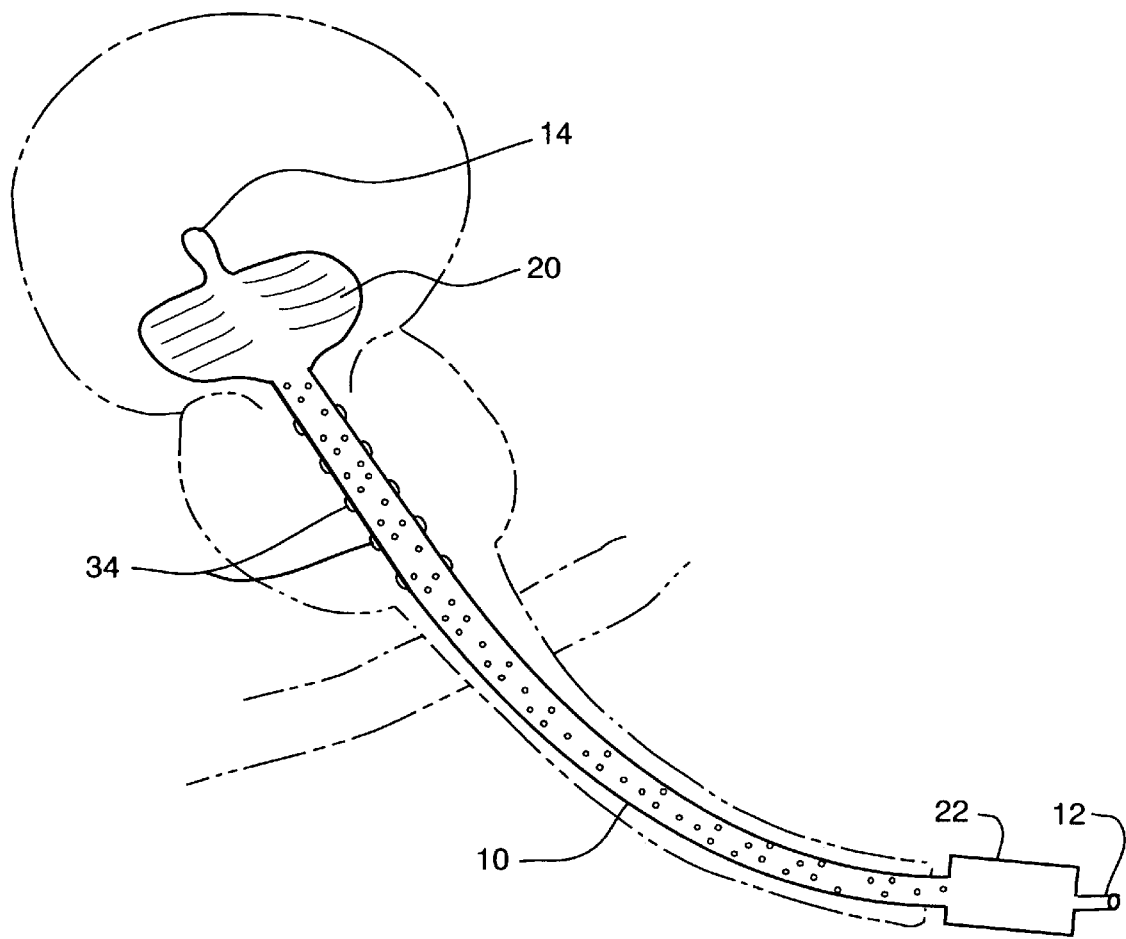
FIG. 2 is a view of the catheter of FIG. 1 in a surgical position.
Figure 3:
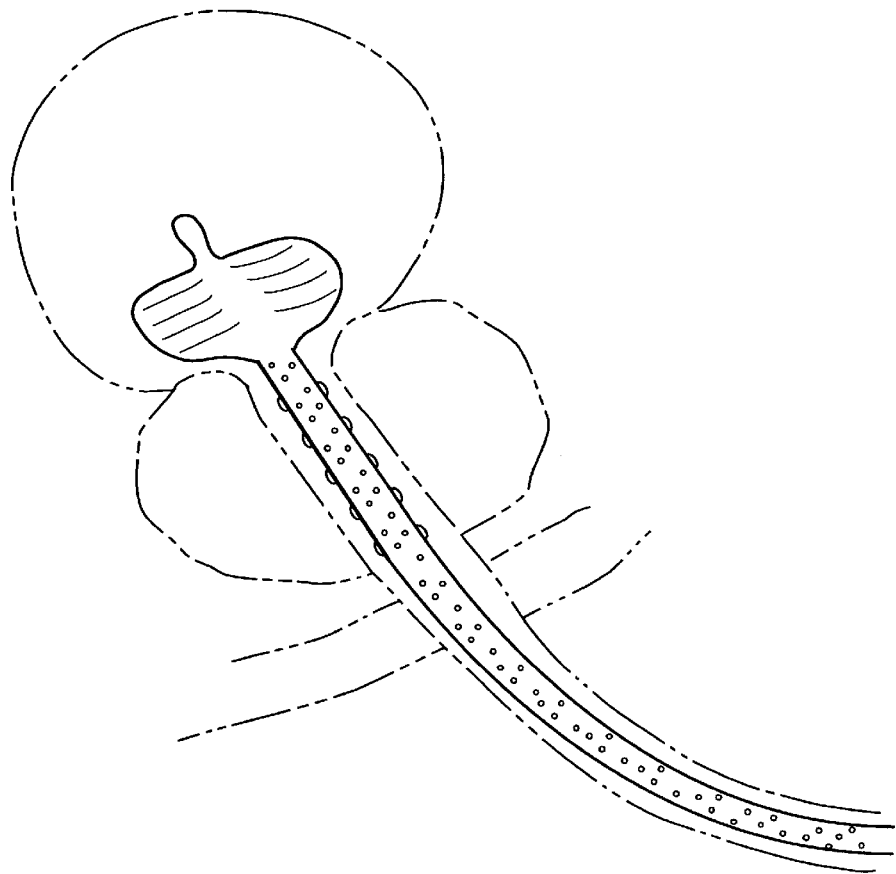
FIG. 3 is a sagittal view of the catheter in the surgical position shown in FIG. 2.

FIG. 2 is a schematic view of the catheter positioned through the urethra and prostatic urethra into the bladder with the balloon inflated. FIG. 3 is a slighly enlarged view of the same prostatic urethra in a sagittal view. FIG. 4 is a cross section of the catheter at the mid point, depicting the lumen containing the semisolid masma of air-filled microspheres, all of which are encompassed within an 18 Fr. external diameter shown as A.

Catheter 10 is 35 cm long and includes an inflatable 5 cubic centimeter (cc) balloon. The balloon preferably initiates about 2 cm from the distal end, continues for 1 cm towards the proximal end, and is preferably inflated with about 5 cc of an inflation medium such as sterile liquids or gases. Suitable fluids include, but are not necessarily limited to, water, saline and radio-opaque contrast. Suitable gases include, but are not limited to, ambient air. The balloon inflation port originates from the proximal end and includes a compressible valve to inflate and deflate the balloon as employed routinely in standard urethral catheters.

The outer surface of the terminal 10 cm of the catheter is ribbed with a plurality of hyperechoic markers 34 at 1 cm increments to facilitate the identification of the length of the posterior (prostatic) urethra.

As noted, the lumen of the catheter contains hypoechoic microspheres. These hypoechoic microspheres are preferably filled with one or more gaseous components; wherein the plurality of microspheres are adapted to appear sufficiently hypoechoic to create an acoustic shadow when viewed by transrectal ultrasound.

Catheter 10 is not adapted to drain any urine, but rather is adapted to serve as an adjunct device to urethral identification by TRUS. However, other suitable adaptations may be designed into the catheter as long as they do not interfere with the primary purpose of the catheter, namely, to facilitate transperineal brachytherapy.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A urethral catheter adapted to facilitate transperineal brachytherapy, comprising, a sleeve having a proximal end, a distal end and at least one lumen at least partially filled with a masma comprising a plurality of hypoechoic microspheres, wherein said sleeve defines an outer wall and an inner wall defining at least said one inner lumen, concentric with said outer wall, that is at least partially filled with said masma comprising said hypoechoic microspheres;

an inflatable balloon fixed about said sleeve proximate said distal end;

an inflation valve proximate said proximal end; and a channel, integral with at least a portion of said sleeve, for transporting an inflation medium from said valve to said balloon.

2. The catheter of claim 1, wherein said channel is interposed between said outer wall and said inner wall.

3. The catheter of claim 1, wherein said plurality of microspheres are adapted to appear sufficiently hypoechoic to create an acoustic shadow when viewed by transrectal ultrasound.

4. The catheter of claim 1, wherein said sleeve further comprises one or more hyperechoic markers between said distal end and said proximal end.

5. The catheter of claim 4, wherein one or more of said hyperechoic markers comprises a circumferential rib integral with said sleeve.

6. The catheter of claim 5, wherein said hyperechoic markers are provided at 1 centimeter intervals.

7. The catheter of claim 1, wherein said inflation medium comprises one or more gaseous components.

8. The catheter of claim 1, wherein said inflation medium comprises one or more fluids.

9. The catheter of claim 1, wherein said balloon is adapted to be inflated to a volume of about 5 cubic centimeters.

10. The catheter of claim 1, wherein said hypoechoic microspheres are filled with one or more gaseous components.

11. The catheter of claim 1, wherein said catheter is disposable after a single use.

12. The catheter of claim 1, wherein said sleeve comprises latex.

13. A urethral catheter, comprising, a sleeve, adapted for transperineal brachytherapy, having a proximal end, a distal end and at least one lumen at least partially filled with a masma comprising a plurality of microspheres that are hypoechoic when viewed by transrectal ultrasound, wherein said sleeve defines an outer wall and an inner wall defining at least said one inner lumen, concentric with said outer wall, that is at least partially filled with said masma comprising said hypoechoic microspheres;

an inflatable balloon fixed about said sleeve proximate said distal end;

an inflation valve proximate said proximal end; and a channel, integral with at least a portion of said sleeve, for transporting an inflation medium from said valve to said balloon.

* * * * *